United States Patent [19]

Effland et al.

[11] 4,169,095

[45] Sep. 25, 1979

[54] PROCESS FOR PREPARING AMINOALKYLPYRROLOBENZOXAZALKANES

[75] Inventors: Richard C. Effland, Bridgewater; Larry Davis, Flemington, both of N.J.; Wolfgang Schaub, Kelkheim, Fed. Rep. of Germany

[73] Assignee: American Hoechst Corporation, Bridgewater, N.J.

[21] Appl. No.: 893,410

[22] Filed: Apr. 4, 1978

Related U.S. Application Data

[62] Division of Ser. No. 760,507, Jan. 19, 1977, Pat. No. 4,107,074, which is a division of Ser. No. 661,505, Feb. 26, 1976, Pat. No. 4,029,672.

[51] Int. Cl.$^2$ .................. C07D 209/52; C07D 491/04
[52] U.S. Cl. .............................................. 260/326.5 B
[58] Field of Search ................................. 260/326.5 B

[56] References Cited

U.S. PATENT DOCUMENTS 4,107,074  8/1978  Effland et al. ............... 260/326.5 B

*Primary Examiner*—Jose Tovar
*Attorney, Agent, or Firm*—Curtis, Morris & Safford

[57] ABSTRACT

Novel aminoalkylpyrrolobenzoxazalkanes, physiologically tolerable acid addition salts thereof, method of preparing same and novel intermediates in the preparation thereof are described. These compounds are useful as analgesic agents and tranquilizers.

2 Claims, 1 Drawing Figure

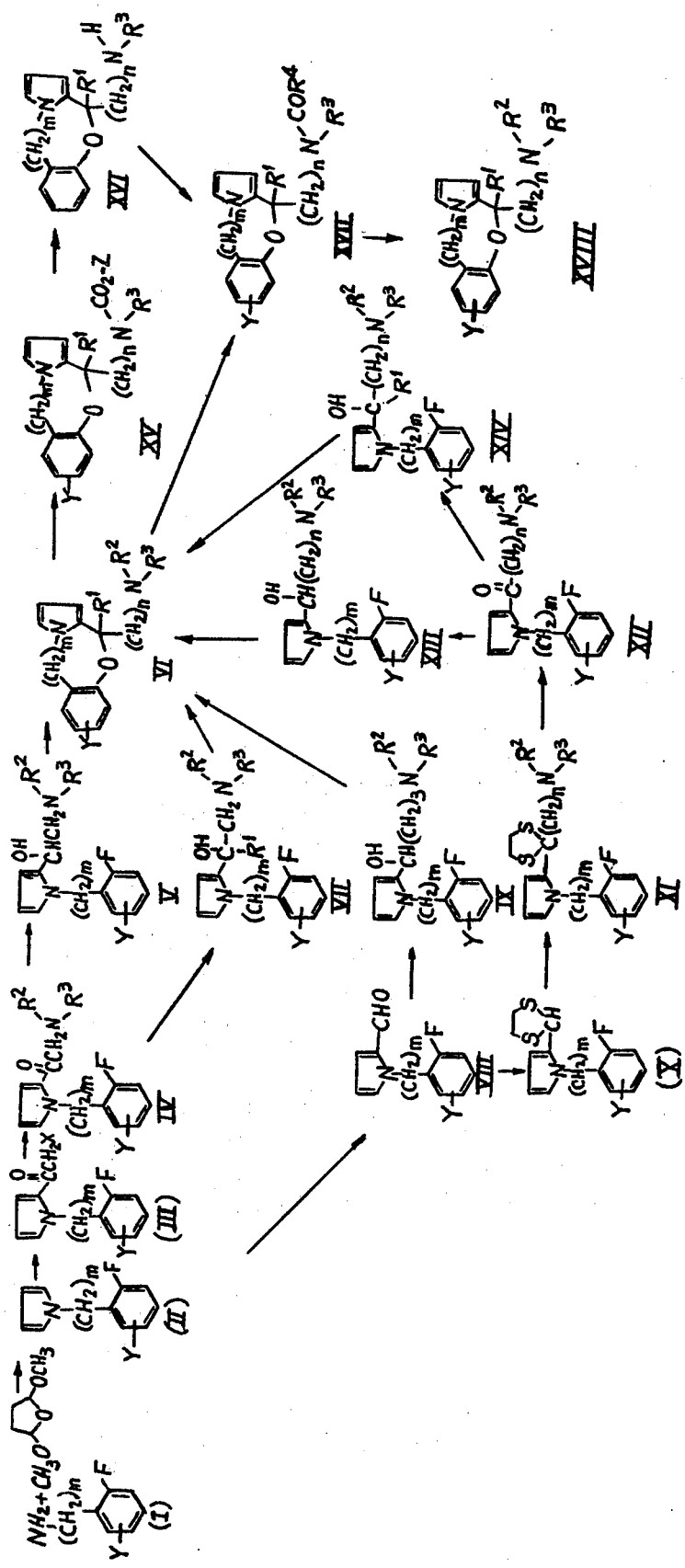

PROCESS FOR PREPARING AMINOALKYLPYRROLOBENZOXAZALKANES

This is a division of application Ser. No. 760,507, filed Jan. 19, 1977, now U.S. Pat. No. 4,107,074, issued Aug. 15, 1978, which was a divisional of Application Ser. No. 661,505 filed Feb. 26, 1976, now U.S. Pat. No. 4,029,672.

This invention relates to novel aminoalkylpyrrolobenzoxazalkanes and to their acid addition salts which are useful as analgesics, to methods of treatment with pharmaceutically effective amounts thereof and to pharmaceutical compositions containing such compounds as essential active ingredients. Additionally, compounds of the invention are further useful as tranquilizers and anticonvulsants. Also described are novel intermediates useful in the preparation of compounds of the invention.

To the best of our knowledge, the compounds of this invention have not heretofore been described or suggested. The compounds herein disclosed represent a new tricyclic ring structure and display significant pharmacological activity as analgesics, anticonvulsants and tranquilizers.

The compounds of the present invention conform to the formula

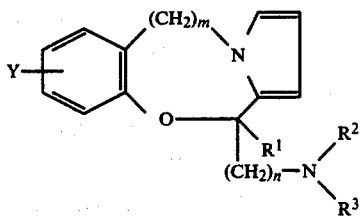

wherein Y is hydrogen, halogen, lower alkoxy, lower alkyl, trifluoromethyl, nitro or amino; $R^1$ is hydrogen or lower alkyl; $R^2$ is hydrogen, alkyl of from 1 to 5 carbon atoms, phenyl, cycloalkyl of from 3 to 6 carbon atoms, phenalkyl of the formula $C_6H_5(CH_2)_n$—, or cycloalkylalkyl of from 4 to 7 carbon atoms; $R^3$ is alkyl of from 1 to 5 carbon atoms, phenyl, cycloalkyl of from 3 to 6 carbon atoms, phenylalkyl of the formula $C_6H_5(CH_2)_n$— or cycloalkyl alkyl of from 4 to 7 carbon atoms; m is the integer 1 or 2 and n is the integer 1, 2 or 3; and the acid addition salts thereof. In the above definitions, halogen means chlorine, iodine, fluorine and bromine; lower alkyl and lower alkoxy mean those radicals of from 1 to 4 carbon atoms and alkyl means straight and branched chain hydrocarbons.

Preferred embodiments of the invention are those compounds wherein m is 1. Also preferred are those compounds in which $R^1$ is hydrogen.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, furmaric and oxalic acids.

The compounds of the present invention are prepared by the several methods of preparation which are outlined below and illustrated in the attached flow sheet. When mentioned below or in the flow sheet, n, m, $R^1$, $R^2$, $R^3$ and Y are, with exceptions noted, as defined earlier and X is chlorine or bromine. $R^4$ is as defined in Method G.

METHOD A

1. An orthofluorophenylalkylamine (I) is reacted with 2,5-dimethoxytetrahydrofuran to produce an orthofluorophenylalkyl pyrrole (II).

Compounds of formula (I) wherein m is 1 can be obtained by brominating a 2-fluorotoluene to produce a 2-fluorobenzylbromide; reacting the 2-fluorobenzylbromide with potassium phthalimide by a Gabriel's synthesis to form a corresponding N-benzyl-phthalimide and cleaving the phthalimide by thermal addition of hydrazine to form a 2-fluorobenzylamine of formula (I).

Compounds of formula (I) wherein m is 2 can be obtained by chlorinating a 2-fluorotoluene to produce a 2-fluorobenzylchloride reacting the benzyl chloride with sodium cyanide to form a corresponding benzyl cyanide and reducing the cyano radical with diborane to produce a 2-fluorophenethylamine of formula (I).

2. An orthofluorophenylalkylpyrrole is allowed to react with a halogenated acetonitrile such as chloroacetonitrile in the presence of an organic solvent which is inert under the reaction conditions at a cooled temperature, preferably 0°-5° C., and the reaction solution is saturated with hydrogen chloride gas to form the corresponding ketimine. The ketimine is subjected to hydrolysis to form the corresponding haloketone (III). A preferred organic solvent for carrying out the reaction is ether.

3. A pyrrylaminoketone (IV) is prepared by the reaction of a haloketone with a mono or disubstituted amine according to the method described by Teotino et al. in U.S. Pat. No. 3,706,750.

4. An above pyrrylaminoketone is reduced to its corresponding pyrrylaminoethanol (V) by a method known to the art such as the method described by Teotino et al. in U.S. Pat. No. 3,539,589. A preferred method utilizes sodium borohydride as the reducing agent and carrying out the reduction in isopropyl alcohol at a temperature of from ambient to the reflux point of the reaction solution.

5. The reaction of a pyrrylaminoethanol with a suitable base produces a tricyclic compound of the present invention (VI) wherein $R^1$ is hydrogen and n is 1. A preferred method utilizes sodium hydride as the base in the presence of an organic solvent such as dry benzene or dimethylformamide.

METHOD B

1. A pyrrylaminoketone (IV) is reacted with a Grignard reagent of the formula $R^1MgX$ under Grignard conditions and then the reaction mixture is hydrolyzed with ice-water to give a corresponding pyrrylaminoalkanol (VII) wherein $R^1$ is alkyl. Preferred Grignard conditions utilize refluxing ether as the reaction medium.

2. A pyrrylaminoalkanol is treated by the procedure described above in Method A, step 5, to produce a corresponding tricyclic compound of the present invention (VI) wherein $R^1$ is alkyl and n is 1.

METHOD C

1. An aldehyde (VIII) is prepared from the orthofluorophenylalkylpyrrole by a method known to the art. One such method is the Vilsmeier-Haack Reaction described in Berichte 60, 119 (1927).

2. The aldehyde is reacted with a Grignard reagent of the formula $(R^2)(R^3)N(CH_2)_3MgX$ wherein $R^2$ is not hydrogen by a method known to the art to produce a corresponding pyrrylaminobutanol (IX). A preferred method is carrying out the reaction in a combined solvent of ether and benzene at a temperature of 45° C.

3. The pyrrylaminobutanol is treated by the procedure described above in Method A, step 5, to produce a corresponding tricyclic compound of the present invention (VI), wherein $R^2$ is not hydrogen and n is 3.

METHOD D

1. An aldehyde (VIII) in an organic solvent such as chloroform is reacted with 1,3-propanedithiol at about ambient temperature to produce a dithiane (X). The yield and purity of the dithiane is enhanced by addition of hydrogen chloride gas to the reaction mixture at −15° C.

2. The dithiane is dissolved in an organic solvent such as tetrahydrofuran and the solution cooled to about between −80° and −20° C. and reacted with n-butyl lithium. The reaction mixture is maintained at between −80° and −20° C. and a di-substituted aminoalkyl halide of the formula

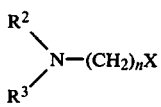

wherein $R^2$ is not hydrogen and n is 2 or 3 are added and the reaction mixture is allowed to react at between about −20° C. and ambient temperature to produce a pyrrylaminodithiane (XI).

3. A pyrrylaminodithiane (XI) is treated with mercuric chloride and acetonitrile in the presence of an acid scavenger such as calcium carbonate and water to produce a corresponding pyrrylpiperazinoketone (XII).

4. A pyrrylaminoketone (XII) is reduced by the procedure described above in method A, step 4 to a pyrrylaminoalkanol (XIII) wherein $R^2$ is not hydrogen and n is 2 or 3 which in turn is treated by the procedure described above in Method A, step 5 to produce a corresponding tricyclic compound of the present invention (VI) wherein $R^2$ is alkyl and n is 2 or 3.

METHOD E

1. A pyrrylaminoketone (XII) is treated by the procedure described above in Method B, step 1 to a corresponding pyrrylaminoalkanol (XIV) wherein $R^1$ is alkyl and n is 2 or 3.

2. An above pyrrylaminoalkanol is treated by the procedure described above in Method A, step 5 to produce a corresponding tricyclic compound of the present invention (VI) wherein $R^1$ is alkyl and n is 2 or 3.

METHOD F

1. A tricyclic compound of the invention wherein $R^2$ is not hydrogen can be reacted in a known manner with a substituted chloroformate to produce a corresponding phenoxy or alkoxycarbonyl compound (XV), a novel intermediate of the present invention wherein Z is phenyl or alkyl. One such method utilizes benzene as a solvent and carrying out the reaction at ambient temperature. An acid scavenger such as sodium bicarbonate can be optionally added to the reaction mixture to remove any hydrogen chloride.

2. The above carbonyl compound is treated with a strong mineral base such as potassium hydroxide in a solvent such as n-propanol to produce a mono substituted amino compound of the invention (XVI).

METHOD G

1. A tricyclic compound of the invention (VI or XVI), wherein $R^2$ is hydrogen can be treated with a carbonyl halide of the formula $R^4$-COX wherein $R^4$ is alkyl, phenyl, phenylalkyl, substituted phenylalkyl, cycloalkyl or cycloalkylalkyl and X is bromine or chlorine to a corresponding N-carbonylamino compound (XVII), a novel intermediate of the present invention.

2. An above N-carbonylamino compound can be reduced in a known manner with a reagent such as lithium aluminum hydride to a corresponding tricyclic compound of the invention (XVIII) wherein $R^2$ is alkyl, phenylalkyl or cycloalkylalkyl.

The compounds of the present invention are useful as analgesic agents due to their ability to alleviate pain in mammals. The analgesic activity of compounds of this invention is demonstrated in the phenyl-2-quinone-induced writhing assay in mice, a standard assay for analgesia [Proc. Soc. Exptl. Biol. Med., 95, 729 (1957)]. Thus, for instance, an approximately 50% inhibition of writhing is effected by 0.78 mg/kg subcutaneous dose of 4-(ethylaminomethyl)-4H,10H-pyrrolo[2,1-c][1,4]benzoxazepine. Similarly effective are oral doses of about 3.2 mg/kg, 8.0 mg/kg, and less than 10.0 mg/kg of 4-(dimethylaminomethyl)-4H,10H-pyrrolo[2,1-c][1,4]benzoxazepine, 4-(methylaminomethyl)-4H,10H-pyrrolo[2,1-c]-[1,4]benzoxazepine and 4-(diethylaminomethyl)-4H,10H-pyrrolo[2,1-c]-[1,4]benzoxazepine hydrochloride, respectively. For comparison, aspirin and propoxyphene hydrochloride, known analgesic agents, effect a 34% and 50% inhibition of writhing with doses of 60 mg/kg and 28 mg/kg, respectively. These data illustrate that the tricyclic compounds of this invention are useful for the alleviation of pain in mammals when administered in amounts ranging from about 0.1 to about 100 mg/kg of body weight per day.

Compounds of the present invention are further useful as tranquilizers due to their depressant action on the central nervous system of mammals. This activity is demonstrated in the mouse observation procedure, a standard assay for CNS depressants [Psychlopharmacologia, 9, 259 (1966)]. Thus, for instance, the minimum effective dose (MED) at which 4-(ethylaminomethyl)-4H,10H-pyrrolo[2,1-c][1,4]benzoxazepine and 4-(diethylaminomethyl)-4H,10H-pyrrolo[2,1-c][1,4]benzoxazepine hydrochloride display significant effects on behavior and reflex depression together with muscle relaxation is 10 mg/kg. This data illustrates that compounds of the present invention are useful as tranquilizers in mammals when administered in amounts ranging from about 0.1 to 100 mg/kg of body weight per day.

Compounds of the present invention are still further useful as anticonvulsant agents for mammals, as determined by the method of Woodbury, L. A. and Davenport, V. D., in Arch. Int. Pharmacodynam, Vol. 92, (1952) at pages 97–107. For example, intraperitoneal doses of 25 mg/kg of 4-(ethylaminomethyl)-4H,10H-pyrrolo[2,1-c][1,4]benzoxazepine, 18 mg/kg of 4-(diethylaminomethyl)-4H,10H-pyrrolo[2,1-c][1,4]benzoxazepine hydrochloride and 36 mg/kg 4-(methylaminomethyl)-4H,10H-pyrrolo[2,1-c][1,4]benzoxazepine produce a 67%, 50% and 50% protection from the effect of supra maximal electro shock, respectively. This data illustrates the utility of compounds of the invention for the treatment of convulsion in mammals when administered in amounts ranging from about 0.1 to 100 mg/kg of body weight per day.

Further examples of compounds of the invention are:
4-(cyclohexylaminomethyl)-4H,10H-pyrrolo[2,1-c][1,4]benzoxazepine;
6-methoxy-4-(diethylaminomethyl)-4H,10H-pyrrolo[2,1-c][1,4]benzoxazepine;
7-ethyl-4-(isopropylaminomethyl)-4H,10H-pyrrolo[2,1-c][1,4]benzoxazepine;
10,11-dihydro-6-methyl-4-(dimethylaminoethyl)-4H-pyrrolo[2,1-c][1,4]benzoxazocine;
4-butyl-4-(diethylaminopropyl)-4H,10H-pyrrolo[2,1-c][1,4]benzoxazepine;
4-(diphenylaminoethyl)-4H,10H-pyrrolo[2,1-c][1,4]benzoxazepine;
4-(dimethylaminopropyl)-9-trifluoromethyl-4H,10H-pyrrolo[2,1-c][1,4]benzoxazepine;
10,11-dihydro-4-ethyl-4-(isopropylaminopropyl)-4H-pyrrolo[2,1-c][1,4]benzoxazocine;
4-(dimethylaminoethyl)-6-nitro-4H,10H-pyrrolo[2,1-c][1,4]benzoxazepine;
7-amino-4-(cyclopropylmethylaminomethyl)-4H,10H-pyrrolo[2,1-c][1,4]benzoxazepine; and
4-(benzylaminopropyl)-4H,10H-pyrrolo[2,1-c][1,4]benzoxazepine.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutics administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is further illustrated by the following examples.

EXAMPLE 1 a. A solution of 40 g of 1-(o-fluorobenzyl)pyrrole and 17.2 g of chloroacetonitrile in 200 ml of anhydrous ether at a temperature between 0° and −5° C. is saturated with hydrogen chloride gas and then the solution is stirred until a heavy white cake forms. This cake is broken up and permitted to sit for one hour at ambient temperature. The white solid is filtered, washed with ether and dried and then hydrolyzed in water and extracted with ether. Concentration of the ether extracts leaves white crystals, mp 76°–78° C., of 2-chloroacetyl-1-(o-fluorobenzyl)pyrrole. The analagous treatment of o-fluorophenethylpyrrole produces 2-chloroacetyl-1-(o-fluorophenethyl)pyrrole.

b. Ethylamine is bubbled into a solution of 57.3 g of 2-chloroacetyl-1-(o-fluorobenzyl)pyrrole and 23.0 g of triethylamine in 400 ml of methanol over a 7 hour span. The methanol is evaporated off leaving an orange semisolid which is washed with water and extracted with ether. The combined ether extracts are washed with water, dried and the ether removed leaving an orange oil which is treated with ethereal hydrogen chloride to produce a crystalline hydrochloride salt. The salt is recrystallized from an ethyl acetate-methanol mixture leaving white crystals, mp 178°–179° C., of 1-(o-fluorobenzyl)-2-[(ethylamino)acetyl]pyrrole.hydrochloride. The analagous treatment of 2-chloroacetyl-1-(o-fluorophenethyl)pyrrole produces 1-(o-fluorophenethyl)-2-[(ethylamino)acetyl]pyrrole hydrochloride.

c. A solution of 31.6 g of 1-(o-fluorobenzyl)-2-[(ethylamino)acetyl]pyrrole, free base of step b, in 200 ml of isopropyl alcohol at ambient temperature is added dropwise to a suspension of 9.2 g of sodium borohydride in 200 ml of isopropyl alcohol at ambient temperature. After total addition the mixture is refluxed for 24 hours and the isopropyl alcohol removed in vacuo leaving a semi-solid. The semi-solid is treated with water for thirty minutes and the product extracted with ether and the ether extract is dried and concentrated leaving a crystalline solid which is recrystallized from a hexane-acetone mixture to give white crystals, mp 108°–110° C., of 1-[1-(o-fluorobenzyl)-2-pyrryl]-2-(ethylamino)ethanol. The analagous reduction and treatment of the free base of 1-(o-fluorophenethyl)-2-(ethylamino)acetylpyrrole hydrochloride produces 1-[1-(o-fluorophenethyl)-2-pyrryl]-2-(ethylamino)ethanol.

d. A mixture of 14.5 g of 1-[1-(o-fluorobenzyl)-2-pyrryl]-2-(ethylamino)ethanol and 2.7 g of 57% sodium hydride in 200 ml of dimethylformamide under nitrogen at 70° C. is stirred for 6 hours. The resulting dark brown solution is poured into 2.5 l of ice-water and treated with 5 ml of ammonium chloride solution. This mixture is allowed to stand for 20 hours and the resulting precipitate is filtered and recrystallized four times from hexane to give the solid, mp 60°–61.5° C., of 4-(ethylaminomethyl)-4H,10H-pyrrolo[2,1-c][1,4]benzoxazepine.

Analysis:
Calculated for $C_{15}H_{18}N_2O$: 74.35%C; 7.49%H; 11.56%N. Found: 74.21%C; 7.54%H; 11.55%N.

The condensation and treatment of 1-[1-(o-fluorophenethyl)-2-pyrryl]-2-(ethylamino)ethanol in analagous fashion produces 10,11-dihydro-4-(ethylaminomethyl)-4H-pyrrolo [2,1-c][1,4]benzoxazocine.

EXAMPLE 2 a. Methylamine is bubbled into a solution of 22.7 g of 2-chloroacetyl-1-(o-fluorobenzyl)pyrrole, Example 1a, and 9.1 g of triethylamine in 140 ml of methanol over an 8 hour span. The solution is refluxed until the reaction ceases and then stirred at ambient temperature for 14 hours. The methanol is evaporated off leaving an orange semi-solid which is treated with water and extracted with methylene chloride. The extract is dried and the solvent removed leaving an orange oil which is acidified with ethereal hydrogen chloride to produce a crystalline hydrochloride salt. The salt is recrystallized from an ethyl acetate-methanol mixture to give light tan colored crystals, mp 185°–186° C., of 1-(o-fluorobenzyl)-2-[(2-methylamino)acetyl]pyrrole.hydrochloride.

b. A solution of 6.4 g of 1-(o-fluorobenzyl)-2-[(2-methylamino)acetyl]pyrrole, free base of a, in 70 ml of isopropyl alcohol is added dropwise to a suspension of 2.0 g of sodium borohydride in 70 ml of isopropyl alcohol at ambient temperature. The resulting mixture is refluxed for 24 hours, the isopropyl alcohol removed in vacuo leaving a semi-solid. The semi-solid is treated with water for thirty minutes and extracted with ether. The ether extract is dried and the ether removed leaving a crystalline solid which is recrystallized from a hexane-acetone mixture to give 1-[1-(o-fluorobenzyl)-2-pyrryl]-2-(methylamino)ethanol.

c. To a stirring solution under nitrogen of 3.1 g of 1-[1-(o-fluorobenzyl-2-pyrryl]-2-(methylamino)ethanol in 40 ml of dimethylformamide at ambient temperature is added portionwise 0.74 g of 57% sodium hydride. The reaction mixture is heated slowly with stirring until the temperature is 70° C. and then stirring at this temperature is maintained for 5 hours. The mixture is allowed to cool to ambient temperature and is poured into ice-water to effect a crystalline product after stirring and rubbing. The product is filtered, washed with water, chromatographed on silica and eluted with chloroform and then a chloroform-ethanol mixture to yield crystals. The crystals were combined and recrystallized from hexane to give white crystals, mp 78°–79° C., of 4-(methylaminomethyl)-4H,10H-pyrrolo[2,1-c][1,4]benzoxazepine.

Analysis:
Calculated for $C_{14}H_{16}N_2O$: 73.66%C; 7.07%H; 12.27%N. Found: 73.84%C; 7.12%H; 12.32%N.

EXAMPLE 3 a. Dimethylamine is bubbled into a solution of 2-chloroacetyl-1-(o-fluorobenzyl)pyrrole, Example 1a, and 10.1 g of triethylamine in 100 ml of methanol at ambient temperature over an 8 hour span. The reaction solution is stirred for 14 hours. The solvent is removed leaving an orange semi-solid which is treated with water and extracted into methylene chloride. The extract is dried and the solvent removed leaving an orange oil. The oil is acidified with ethereal-hydrogen chloride to effect a crystalline hydrochloride salt which is recrystallized from an ethyl acetate-methanol mixture to yield white crystals, mp 194°–195° C., of 1-(o-fluorobenzyl)-2-(dimethylaminoacetyl)pyrrole.hydrochloride.

b. The reduction and treatment of 1-(o-fluorobenzyl)-2-(dimethylaminoacetyl)pyrrole, free base of a, by the procedure of Example 2b produces 1-[1-(o-fluorobenzyl)-2-pyrryl]-2-(dimethylamino)ethanol as an oil. The oil is distilled to effect the product as a colorless oil, bp 146° C./0.3 mm.

c. A solution of 9.6 g of 1-[1-(o-fluorobenzyl)-2-pyrryl]-2-(dimethylamino)ethanol in 60 ml of dimethylformamide is added portionwise under nitrogen to a stirred suspension of 1.84 g of 57% sodium hydride in dimethylformamide. The reaction is maintained at ambient temperature for 30 minutes and then is slowly raised to 70° C. with stirring and stirring is continued at this elevated temperature for 4 hours. The mixture is permitted to cool to ambient temperature and then poured into ice-water. Upon rubbing the aqueous mixture crystals appear which are filtered off, washed with water, dried and recrystallized from petroleum ether to leave a white solid, mp 59°–60.5° C., of 4-(dimethylaminomethyl)-4H,10H-pyrrolo[2,1-c][1,4]benzoxazepine.

Analysis:
Calculated for $C_{15}H_{18}N_2O$: 74.35%C; 7.49%H; 11.56%N. Found: 74.18%C; 7.65%H; 11.49%N.

EXAMPLE 4 a. A mixture of 18.9 g of 2-chloroacetyl-1-(o-fluorobenzyl)pyrrole, Example 1a, and 22.0 g of diethylamine in 65 ml of methanol is stirred at ambient temperature for 24 hours. The methanol is removed in vacuo leaving a dark semi-solid which is acidified in dilute hydrochloric acid and washed with ether. The aqueous phase is basified with a saturated sodium carbonate solution and extracted with ether. The ether extract is washed with a saturated sodium chloride solution, treated with charcoal and dried. The ether is removed leaving a reddish oil which upon distillation leaves a light yellow oil, bp 140° C./0.05 mm, of 2-(diethylaminoacetyl)-1-(o-fluorobenzyl)pyrrole.

b. A solution of 23.0 g of 2-(diethylaminoacetyl)-1-(o-fluorobenzyl)pyrrole in 75 ml of isopropyl alcohol is added portionwise to a stirred suspension of 6.04 g of sodium borohydride in isopropyl alcohol at ambient temperature. After total addition the reaction mixture is refluxed for 14 hours. The isopropyl alcohol is removed in vacuo leaving an orange semi-solid which is treated consecutively with water, a saturated sodium chloride solution and charcoal, and dried. The ether is removed leaving a yellow oil which is distilled (170° C./0.45 mm) to give a light yellow oil which upon standing in the cold solidifies to a light yellow solid, mp 28°–29.5° C., of 2-(diethylamino)-1-[1-(o-fluorobenzyl)-2-pyrryl]ethanol.

c. A solution of 7.26 g of 2-(diethylamino)-1-[1-(o-fluorobenzyl)-2-pyrryl]ethanol in 15 ml of dimethylformamide is added portionwise at ambient temperature under nitrogen to a suspension of 1.16 g of 57% sodium hydride in 25 ml of dimethylformamide. After total addition the reaction mixture is permitted to sit for 1 hour at ambient temperature and then at 70° C. for 5 additional hours. The mixture is cooled to ambient temperature and poured over ice. The resulting aqueous mixture is extracted with benzene, the benzene extract washed consecutively with water and a saturated sodium chloride solution and dried. The benzene solution is treated with charcoal, filtered and the benzene removed leaving a pale yellow oil which is dissolved in ether and cooled. The addition of ethereal-hydrogen chloride with stirring to the cool solution effects a salt as a white solid which is filtered off and washed twice by stirring in acetone to give a pale yellow solid, mp 159°–160° C., of 4-(diethylaminomethyl)-4H,10H-pyrrolo[2,1-c][1,4]benzoxazepine.

Analysis:
Calculated for $C_{17}H_{22}N_2O.HCl$: 66.53%C; 7.57%H; 9.13%N. Found: 66.58%C; 7.56%H; 9.20%N.

EXAMPLE 5 a. A mixture of 20.0 g of 2-chloroacetyl-1-(o-fluorobenzyl)pyrrole, Example 1a, 7.0 g of cyclopropylamine and 12.0 g of triethylamine in 150 ml of methanol is stirred for 4 hours at 50° C. and then at ambient temperature for 20 additional hours. The methanol is removed leaving an orange semi-solid which is treated with water and then extracted into ether. The ether extract is washed with water, dried and filtered and the ether removed leaving an orange oil. The oil is converted to a hydrochloride salt which is recrystallized from an ethylacetate-methanol mixture to yield a solid product, mp 185°–187° C., of 2-[(cyclopropylamino)acetyl]-1-(o-fluorobenzyl)pyrrole.hydrochloride.

b. A solution of 8.0 g of 2-(2-cyclopropylamino)-acetyl-1-(o-fluorobenzyl)pyrrole, free base of a, in 100 ml of isopropyl alcohol is added to a suspension of 2.2 g sodium borohydride in 100 ml of isopropranol. The reaction mixture is refluxed at 85° C. for 4 hours, allowed to cool to ambient temperature and 50 ml of methanol introduced. The solvent is removed leaving a yellow semi-solid which is treated with water and then extracted into ether. The ether extract is washed with water, dried and filtered and the solvent removed leaving a pure yellow oil of 2-(cyclopropylamino)-1-[1-(o-fluorobenzyl)-2-pyrryl]ethanol. Infrared and nuclear magnetic resonance spectra confirm this structure.

c. A solution of 6.5 g of 2-(cyclopropylamino)-1-[1-(o-fluorobenzyl)-2-pyrryl]ethanol in 100 ml of benzene is added to a suspension of 50% sodium hydride in 50 ml of benzene. The mixture is heated to reflux, then 25 ml of dimethylformamide added and the temperature is maintained at 85° C. for 5 hours. The reaction mixture is permitted to cool to ambient temperature and poured into 500 ml water. The aqueous mixture is stirred for 10 minutes and then extracted with ether. The combined organic extracts are washed with water, dried and filtered and the solvent removed leaving a dark oil. The oil is dissolved in ether and converted to its oxalate salt which is recrystallized from a methanol-ether mixture to provide the solid product, mp 150° C. dec., of 4-(cyclopropylaminomethyl)-4H,10H-pyrrolo[2,1-c][1,4]benzoxazepine.oxalate.

Analysis:
Calculated for $C_{16}H_{18}N_2O.(CO_2H)_2$: 62.78%C; 5.85%H, 8.13%N. Found: 62.64%C; 6.00%H; 8.08%N.

EXAMPLE 6 a. A mixture of 19.0 g of 2-chloroacetyl-1-(o-fluorobenzyl)pyrrole, Example 1a, 7.05 g of n-propylamine and 12.0 g of triethylamine in 150 ml of methanol is stirred at ambient temperature for 20 hours and at 60° C. for 4 additional hours. The mixture is allowed to cool and the solvent removed leaving a brown oil which is treated with water and extracted into ether. The ether extract is washed with water, dried and filtered and the solvent removed again leaving a brown oil. The oil is converted to a hydrochloride salt which is recrystallized from an ethyl acetate-methanol mixture to yield the salt, mp 135°–137° C., of 1-(o-fluorobenzyl)-2-[(n-propylamino)acetyl]pyrrole.hydrochloride.

b. The reduction and treatment of 1-(o-fluorobenzyl)-2-[(2-propylamino)acetyl]pyrrole, free base of a, by the procedure of Example 5b produces a pure brown oil of 1-[1-(o-fluorobenzyl)-2-pyrryl]-2-(propylamino)ethanol. Infrared and nuclear magnetic resonance spectra confirm this structure.

c. The condensation and treatment of 1-[1-(o-fluorobenzyl)-2-pyrryl]-2-(propylamino)ethanol by the procedure of Example 5c produces the oxalate salt, mp 170° C. dec., of 4-(propylaminomethyl)-4H,10H-pyrrolo[2,1-c][1,4]-benzoxazepine.

Analysis:
Calculated for $C_{16}H_{20}N_2O.(CO_2H)_2$: 62.42%C; 6.40%H; 8.09%N. Found: 62.24%C; 6.65%H; 7.92%N.

EXAMPLE 7 a. A mixture of 16.0 g of 2-chloroacetyl-1-(o-fluorobenzyl)pyrrole, Example 1a, 8.3 g of di-sec-butylamine and 20.0 g of potassium carbonate in 250 ml xylene is stirred at 120° C. for 72 hours. The mixture is cooled, washed with water, dried and filtered and the xylene is evaporated leaving a brown oil. The oil is dissolved in ether and extracted into a 2 N hydrogen chloride solution. The aqueous acidic solution is basified with a sodium carbonate solution and extracted with ether. The ether solution is washed, dried and filtered and the ether removed leaving a brown oil of 1-(o-fluorobenzyl)-2[(di-sec-butylamino)acetyl]-pyrrole. Infrared and nuclear magnetic resonance spectra confirm this structure.

b. The above acetyl compound is added to a suspension of 1.33 g of sodium borohydride in 200 ml of isopropyl alcohol. The reaction mixture is refluxed for 20 hours, allowed to cool to ambient temperature and the solvent removed leaving a white semi-solid which is treated with water and extracted into ether. The ether extract is washed with water, dried and filtered and the solvent removed leaving 1-[1-(o-fluorobenzyl)-2-pyrryl]-2-(di-sec-butylamino)ethanol as a brown oil. Infrared and nuclear magnetic resonance spectra confirm this structure.

c. A solution of 7.0 g of 1-[1-(o-fluorobenzyl)-2-pyrryl]-2-(di-sec-butylamino)ethanol in 100 ml of benzene is added to a suspension of 50% sodium hydride in 50 ml of benzene. The mixture is heated to reflux, 30 ml of dimethylformamide is added and refluxing continued for 4 hours. The reaction mixture is allowed to cool, poured into water and the biphasic mixture is stirred for 15 minutes and extracted with ether. The combined organic extracts are washed with water, dried and filtered and the solvent removed leaving a brown oil. The oil is dissolved in ether and converted to its hydrochloride salt which is recrystallized from an ethyl acetate-methanol mixture to yield the solid product, mp 130° C. dec., of 4-(di-sec-butylaminomethyl)-4H,10H-pyrrolo[2,1-c][1,4]benzoxazepine.hydrochloride.

Analysis:
Calculated for $C_{21}H_{30}N_2O \cdot HCl$: 69.49%C; 8.61%H; 7.72%N. Found: 69.28%C; 8.62%H; 7.67%N.

EXAMPLE 8 a. A mixture of 12.0 g of 2-chloroacetyl-1-(o-fluorobenzyl)pyrrole, Example 1a, 9.0 g of aniline, and 9.0 g of triethylamine in 100 ml of n-butanol is stirred at 120° C. for 24 hours. The mixture is allowed to cool to ambient temperature and the n-butanol removed leaving a brown oil. The oil is treated with water and extracted with ether. The combined ether extracts are washed with water, dried and filtered. Any residual unreacted aniline is selectively precipitated as the oxalate salt. The ether solution is evaporated leaving a yellow solid which is recrystallized from petroleum ether to give the product, mp 74°–75° C., of 2-(2-anilinoacetyl)-1-(o-fluorobenzyl)pyrrole.

b. The reduction and treatment of 2-(2-anilinoacetyl)-1-(o-fluorobenzyl)pyrrole by the procedure of Example 5b produces 2-anilino-1-[1-(o-fluorobenzyl)-2-pyrryl]ethanol as a brown oil. Infrared and nuclear magnetic resonance spectra confirm this structure.

c. The condensation and treatment of 2-anilino-1-[1-(o-fluorobenzyl)-2-pyrryl]ethanol by the procedure of Example 5c produces a brown oil which is converted to a hydrochloride salt and recrystallized from a methanol-ether mixture to give the solid, mp 140° C., dec., of 4-anilino-4H,10H-pyrrolo[2,1-c][1,4]benzoxazepine.hydrochloride.

Analysis:
Calculated for $C_{19}H_{18}N_2O \cdot HCl$: 69.82%C; 5.86%H; 8.57%N. Found: 69.56%C; 5.90%H; 8.52%N.

EXAMPLE 9 a. A solution of (4-chloro-2-fluorobenzyl)pyrrole and chloroacetonitrile in ether is treated by the procedure described in Example 1a to produce 2-chloroacetyl-1-(4-chloro-2-fluorobenzyl)pyrrole.

b. A mixture of 14.3 g of 2-chloroacetyl-1-(4-chloro-2-fluorobenzyl)pyrrole, 3.65 g of diethylamine and 5.05 g of triethylamine in 75 ml of methanol is stirred at ambient temperature for 14 hours. To this mixture is added another 3.65 g of diethylamine and 5.05 g of triethylamine and the mixture is stirred at reflux for 3 hours. An additional 1.5 g of diethylamine is added and stirring and refluxing is continued for 2 hours. After the mixture is allowed to cool the methanol is removed leaving an orange semi-solid which is treated with water and extracted into ether. The ether extract is dried and the ether evaporated in vacuo leaving an orange oil. The oil is dissolved in ether, the ether solution is filtered and then acidified with ethereal hydrogen chloride to effect a salt as a crystalline precipitate. The salt is recrystallized from an ethyl acetate-methanol mixture to produce white crystals, mp 165°–166° C., of 1-(4-chloro-2-fluorobenzyl)-2-[(diethylamino)acetyl]pyrrole.

c. The reduction and treatment of 1-(4-chloro-2-fluorobenzyl)-2-[(2-diethylamino)acetyl]pyrrole by the procedure described in Example 5b produces a yellow oil of 1-[1-(4-chloro-2-fluorobenzyl)-2-pyrryl]-2-(diethylamino)ethanol. Infrared and nuclear magnetic resonance spectra confirm this structure.

d. A solution of 7.6 g of 1-[1-(4-chloro-2-fluorobenzyl)-2-pyrryl]-2-(diethylamino)ethanol in 100 ml of benzene is added dropwise to a suspension of 50% sodium hydride in 50 ml benzene. After total addition the mixture is heated to reflux, 30 ml of dimethylformamide is added and refluxing continued for 4 hours. The reaction mixture is allowed to cool and then poured into 1 l. of water and stirred for 10 minutes. This mixture is extracted with ether and the combined organic extracts are washed with water, dried, treated with charcoal, filtered and the solvent removed leaving a brown oil. The oil is dissolved in ether and converted to its hydrogen chloride salt which is recrystallized from an ethyl acetate-methanol mixture (9:1) to yield the salt, mp 125° C. dec., of 7-chloro-4-(diethylaminomethyl)-4H,10H-pyrrolo[2,1-c][1,4]benzoxazepine hydrochloride.

Analysis:
Calculated for $C_{17}H_{21}ClN_2O \cdot HCl$: 59.82%C; 6.50%H; 8.21%N. Found: 60.29%C; 6.85%H; 8.31%N.

EXAMPLE 10 a. A solution of 11.0 g of 1-(o-fluorobenzyl)-2-(dimethylaminoacetyl)pyrrole, free base of Example 3a, in ether is added dropwise to a stirring solution of n-propylmagnesium bromide which is prepared from 1.67 g of magnesium turnings and 8.4 g of n-propylbromide. The mixture is refluxed for 4 hours, allowed to cool, hydrolized with ice-water and treated with concentrated ammonium chloride solution to dissolve the magnesium hydroxide precipitate. The organic phase is separated and the aqueous phase extracted with ether and the organic phases are combined, washed with a 5% sodium bicarbonate solution and water and dried. Removal of the ether leaves a crude yellow oil which is distilled at 133°–137° C./0.08 mm gives a light yellow oil of 1-(dimethylamino)-2-[1-(o-fluorobenzyl)-2-pyrryl]-2-hydroxypentane.

b. To a stirred solution of 7.1 g of 1-(dimethylamino)-2-[1-(o-fluorobenzyl)-2-pyrryl]-2-hydroxypentane in 70 ml of dimethylformamide at ambient temperature is added portionwise 1.4 g of 57% sodium hydride. The reaction mixture is carefully heated with stirring to 70° C. over a 1 hour span and stirring is then maintained at this temperature for an additional 5 hours. The mixture is allowed to cool and poured into ice-water to effect an oily product which is extracted into ether. The ether extract is washed with water, dried and the ether removed leaving an oil. The oil is dissolved in ether and the oxalate salt prepared. The salt is recrystallized from an ethyl acetate-methanol mixture to effect grayish crystals, mp 135°–136° C., of 4-(n-propyl)-4-(dimethylaminomethyl)-4H,10H-pyrrolo[2,1-c][1,4]-benzoxazepine.oxalate.

Analysis: Calculated for $C_{18}H_{24}N_2O.(CO_2H)_2$: 64.15%C; 7.00%H; 7.48%N. Found: 64.03%C; 7.06%H; 7.47%N.

EXAMPLE 11 a. A solution of 16.0 g of 1-(o-fluorobenzyl)-2-(dimethylaminoacetyl)pyrrole, free base of Example 3a, in 60 ml of ether is treated with a solution of methylmagnesium iodide, prepared from 2.7 g of magnesium turnings and 15.3 g of methyl iodide, in 40 ml of ether according to the procedure described in Example 9a to produce a crude yellow oil of 1-(dimethylamino)-2-[1-(o-fluorobenzyl)-2-pyrryl]-2-hydroxypropane. Distillation at 130°–138° C./0.1 mm affords the product as a faintly yellow oil.

b. To a solution of 8.3 g of 1-dimethylamino-2-[1-(o-fluorobenzyl)-2-pyrryl]-2-hydroxypropane in 80 ml of dimethylformamide at ambient temperature is added portionwise 1.95 g of 57% sodium hydride. The mixture is carefully heated with stirring to 70° C. over a 1 hour span and stirring is maintained at this temperature for an additional 5 hours. The mixture is allowed to cool and poured into ice-water effecting an oil product which is extracted into ether. The ether extract is washed with water and dried and the solvent removed leaving a crude oil. The oil is purified by column chromatography (silica gel, eluted with ether), dissolved in ether and ethereal malonic acid is added to produce an amorphous malonate salt. This salt is washed well with ether and by the addition of an aqueous sodium carbonate solution the free base is recovered as an oil. The base is dissolved in ether and the oxalate salt prepared which is recrystallized from an ethyl acetate-methanol mixture to afford cream colored crystals, mp 141°–142.5° C., of 4-methyl-4-(dimethylaminomethyl)-4H,10H-pyrrolo[2,1-c][1,4]benzoxazepine.oxalate.

Analysis:
Calculated for $C_{16}H_{20}N_2O.(CO_2H)_2$: 62.42%C; 6.40%N; 8.09%N. Found: 62.19%C; 6.52%N; 8.00%N.

EXAMPLE 12 a. In a 500 ml three neck round bottom flask 8 g of dimethylformamide is cooled to 5° C. and 16.9 g of phosphorous oxychloride is added dropwise with stirring while maintaining the temperature below 20° C. after total addition the mixture is stirred at ambient temperature for 15 minutes, 25 ml of ethylene dichloride introduced and the solution cooled to 5° C. The temperature of the solution is maintained at this low temperature with stirring during the addition of a solution of 17.5 g of 1-(o-fluorobenzyl)pyrrole, Example 1a, in 25 ml of ethylene dichloride. The reaction solution is stirred at this temperature for 30 minutes at ambient temperature for an additional 30 minutes and then refluxed under nitrogen for 5 hours. The mixture is allowed to cool to ambient temperature and a solution of 75 g of sodium acetate.trihydrate in 120 ml of water is added. The two phase mixture is stirred vigorously at ambient temperature for 15 minutes and then refluxed for 30 minutes. After the reaction mixture cools to ambient temperature the ethylene dichloride layer is removed and the aqueous phase is extracted with ether. The combined organic extracts are washed twice with a saturated sodium carbonate solution and once with a saturated sodium chloride solution and dried. Removal of the solvent leaves a light yellow oil which solidifies upon standing to a pale yellow solid which is recrystallized from an ether-hexane mixture to give nearly white crystals, mp 39°–41° C., of 1-(o-fluorobenzyl)pyrrole-2-carboxaldehyde.

b. To 2.4 g of magnesium turnings in 100 ml ether is added one ml dibromoethane and a crystal of iodine. When the reaction starts a solution of 12.1 g of dimethylaminopropyl chloride in 100 ml of ether is added under vigorous reflux over a 15 minute span. After total addition 100 ml of benzene is added and the mixture is refluxed at 45° C. for 1 hour. The mixture is allowed to cool and a solution of 10.0 g of 1-(o-fluorobenzyl)pyrrole-2-carboxaldehyde in 50 ml of ether is added and the mixture is stirred at 45° C. for 20 hours. The reaction is allowed to cool, poured into 1 l. of ammonium chloride solution, stirred for 30 minutes and extracted with chloroform. The chloroform extract is washed well with water, dried and filtered and the solvent removed leaving a tan solid which is recrystallized from ether to leave the solid, mp 99°–101° C., of 1-[1-(o-fluorobenzyl)-2-pyrryl]-4-(dimethylamino)butanol.

c. A solution of 10.4 g of 1-[1-(o-fluorobenzyl)-2-pyrryl]-4-(dimethylamino)butanol in 100 ml of benzene is treated with a suspension of 2.2 g of 50% sodium hydride in 50 ml of benzene according to the procedure described in Example 8d to produce a brown oil. The oil is dissolved in ether and converted to its oxalate salt which is recrystallized from a methanol-ether mixture to afford the compound, mp 155° C. dec., of 4-(dimethylaminopropyl)-4H,10H-pyrrolo[2,1-c]-[1,4]benzoxazepine.oxalate.

Analysis:
Calculated for $C_{17}H_{22}N_2O.(CO_2H)_2$: 63.32%C; 6.71%H; 7.77%N. Found: 63.18%C; 6.90%H; 7.93%N.

EXAMPLE 13

To a cooled solution of 2.8 g of 4-propylaminomethyl-4H,10H-pyrrolo[2,1-c][1,4]benzoxazepine, Example 6c, and 3 ml of triethylamine in 50 ml of chloroform is added a solution of 2.3 g of phenylacetyl chloride in 25 ml of chloroform. The reaction mixture is stirred at ambient temperature for 24 hours, and the mixture is washed, dried and filtered. The solvent is evaporated off leaving a brown oil which is dissolved in 50 ml of tetrahydrofuran and this solution added to a refluxing solution of 1.0 g of lithium aluminum hydride in 100 ml of tetrahydrofuran. The mixture is refluxed at 65° C. for 20 hours, cooled treated with 30 ml of a saturated ammonium chloride solution, filtered and diluted with ether. The combined organic layers are washed with water, dried and filtered and the solvent removed leaving a brown oil. The oil is dissolved in ether and converted to an oxalate salt which is recrystallized from a methanol-ether mixture to give the product, mp 125° C., dec., of 4-(N-phenethyl-N-propylaminomethyl)-4H,10H-pyrrolo[2,1-c][1,4]benzoxazepine.oxalate.

Analysis:
Calculated for $C_{24}H_{28}N_2O.(CO_2H)_2$: 69.31%C; 6.71%H; 6.22%N. Found: 68.73%C; 6.99%H; 6.37%N.

EXAMPLE 14 a. A solution of 25.0 g of 1-(o-fluorobenzyl)-pyrrole-2-carboxaldehyde, Example 12a, and 13.5 g of 1,3-propanedithiol in 200 ml of chloroform is stirred at ambient temperature for 1 hour and the mixture is cooled to −15° C. Hydrogen chloride gas is bubbled into the mixture over a 10 minute span and after stirring the reaction mixture for 20 hours at ambient temperature the mixture is washed successively with water, 10% potassium hydroxide solution, and water and dried. After filtering the solvent is evaporated leaving a yellow solid which is recrystallized twice from hexane to give an off-white solid, mp 105°-106° C., of 2-[1-(o-fluorobenzyl)-2-pyrryl]-1,3-dithiane.

b. To a solution of 25.0 g of 2-[1-(o-fluorobenzyl)-2-pyrryl]-1,3-dithiane in 150 ml tetrahydrofuran at −60° C. is added portionwise a solution of 50 ml of n-butyl lithium in hexane over a 30 minute span. After stirring at −20° C. for 1 hour, the mixture is cooled to −60° C., and 12.4 g of dimethylaminoethyl chloride is added portionwise over a five minute span. The reaction mixture is stirred at −20° C. for six hours and allowed to stand for 14 hours at 5° C. and then stirred at ambient temperature for 4 additional hours. The mixture is filtered and the solvent evaporated off leaving a dark oil, which is converted to an oxalate salt. The salt is reconverted to the free base, purified on a silica gel column and eluted with chloroform to give the base as a solid which is recrystallized from hexane to give the solid, mp ∼55° C., of 2-(2-dimethylaminoethyl)-2-[1-(o-fluorobenzyl)-2-pyrryl]-1,3-dithiane. Infrared and nuclear magnetic resonance spectra confirm this structure.

c. To a solution of 28.1 g of mercuric chloride and 10.3 g of calcium carbonate in 150 ml of aqueous 80% acetonitrile is added under nitrogen a solution of 17.0 g of 2-(2-dimethylaminoethyl)-2-[1-(o-fluorobenzyl)-2-pyrryl]-1,3-dithiane in 100 ml of aqueous 80% acetonitrile. The reaction mixture is stirred at reflux for 4 hours, the mixture is permitted to cool and filtered through celite. The filter cake is washed with a hexane-dichloromethane mixture and the washed solution is washed successively with a 5 M aqueous ammonium acetate solution and water, dried and filtered. The solvents are evaporated off leaving a dark oil which solidifies upon trituration with n-hexane to give the solid product of 2-(3-dimethylaminopropionyl)-1-(o-fluorobenzyl)pyrrole.

d. The reduction of 2-(3-dimethylaminopropionyl)-1-(o-fluorobenzyl)pyrrole by the procedure described in Example 1c produces 1-[1-(o-fluorobenzyl)-2-pyrryl]-2-(3-dimethylamino)-1-propanol.

e. The condensation and treatment of 1-[1-(o-fluorobenzyl)-2-pyrryl]-2-(3-dimethylamino)-1-propanol by the procedure described in Example 1d produces 4-(dimethylaminoethyl)-4H,10H-pyrrolo[2,1-c][1,4]benzoxazepine.

EXAMPLE 15 a. To a solution of 4-(diethylaminomethyl)-4H,10H-pyrrolo[2,1-c][1,4]benzoxazepine and sodium bicarbonate in benzene at ambient temperature is added portionwise phenylchloroformate. The reaction mixture is allowed to stand for five hours and the benzene removed leaving 4-[(N-ethyl-N-phenoxycarbonyl)aminomethyl]-4H,10H-pyrrolo[2,1-c][1,4]-benzoxazepine.

b. To a solution of 4-[(N-ethyl-N-phenoxycarbonyl)-aminomethyl]-4H,10H-pyrrolo[2,1-c][1,4]benzoxazepine in n-propanol is added potassium hydroxide solution and the reaction mixture allowed to stand for 5 hours. The mixture is washed and dried and the solvent removed leaving 4-(ethylamino-methyl)-4H,10H-pyrrolo[2,1-c][1,4]benzoxazepine.

We claim:

1. A process for the preparation of an aminoalkylpyrrolobenzoxazalkane of the formula

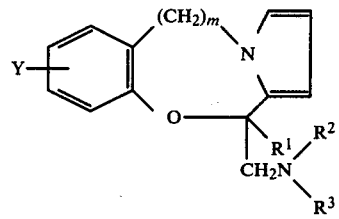

wherein Y is hydrogen, halogen, lower alkoxy, lower alkyl, trifluoromethyl, nitro or amino; $R^1$ is hydrogen or lower alkyl; $R^2$ is hydrogen, alkyl of from 1 to 5 carbon atoms, phenyl, cycloalkyl of from 3 to 6 carbon atoms, phenalkyl of the formula $C_6H_5(CH_2)_n-$, or cycloalkylalkyl of from 4 to 7 carbon atoms; $R^3$ is alkyl of from 1 to 5 carbon atoms, phenyl, cycloalkyl of from 3 to 6 carbon atoms, phenylalkyl of the formula $C_6H_5(CH_2)_n-$ or cycloalkylalkyl of from 4 to 7 carbon atoms; m is the integer 1 or 2 and n is the integer 1, 2 or 3; which comprises reacting an orthofluorophenylalkylpyrrole of the formula

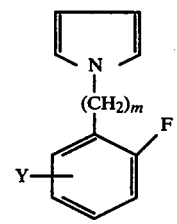

with a halogenated acetonitrile in the presence of an organic solvent which is inert under the reaction conditions at a cooled temperature and introducing hydrogen chloride gas into the reaction solution forming a ketimine; hydrolyzing said ketimine to produce a haloketone of the formula

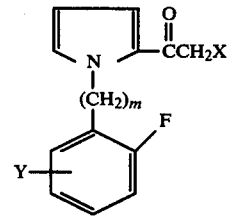

wherein X is chlorine or bromine; reacting said haloketone with an amine of the formula $H_2NR^2R^3$ at a temperature of from ambient to 150° C. in the presence of an acid scavenger to produce a pyrrylamino ketone of the formula

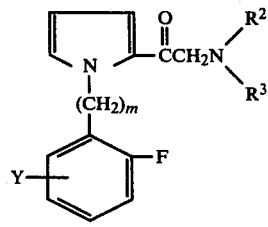

reducing said pyrrylamino ketone to a pyrrylamino ethanol of the formula
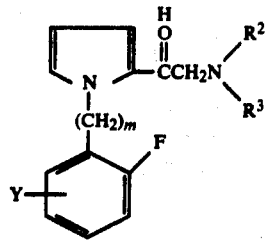
and reacting said pyrrylamino ethanol with a mineral base to effect condensation to said aminoalkylpyrrolobenzoxazalkane.
2. The process according to claim 1 wherein the mineral base effecting condensation of said pyrrylamino ethanol is sodium hydride.